US008603345B2

(12) United States Patent
Ross et al.

(10) Patent No.: US 8,603,345 B2
(45) Date of Patent: Dec. 10, 2013

(54) DEVICES FOR COMPONENT REMOVAL DURING BLOOD COLLECTION, AND USES THEREOF

(75) Inventors: Julie Ross, Rydal, PA (US); Bruce Haywood, Franklin Lakes, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1080 days.

(21) Appl. No.: 10/544,886

(22) PCT Filed: Feb. 13, 2004

(86) PCT No.: PCT/US2004/002019
§ 371 (c)(1),
(2), (4) Date: Mar. 3, 2006

(87) PCT Pub. No.: WO2004/073864
PCT Pub. Date: Sep. 2, 2004

(65) Prior Publication Data
US 2007/0020629 A1 Jan. 25, 2007

Related U.S. Application Data

(60) Provisional application No. 60/447,014, filed on Feb. 13, 2003.

(51) Int. Cl.
*B01D 21/26* (2006.01)
*C12Q 1/68* (2006.01)
*G01N 33/53* (2006.01)
(52) U.S. Cl.
USPC ..... 210/789; 210/787; 210/502.1; 210/512.1; 435/6.1; 435/7.1; 436/177; 530/413

(58) Field of Classification Search
USPC .......... 210/656, 660, 198.2, 502.1, 504, 506, 210/782, 787, 789, 512.1; 435/2, 6, 7.1, 435/395, 396, 402, 304.1, 287.2, 6.1; 436/177, 178; 530/412, 413, 417; 604/403, 415, 416
See application file for complete search history.

(56) References Cited

U.S. PATENT DOCUMENTS

| | | | | |
|---|---|---|---|---|
| 3,646,346 A | * | 2/1972 | Catt | 436/531 |
| 3,882,225 A | * | 5/1975 | Patel et al. | 436/519 |
| 3,894,952 A | * | 7/1975 | Ayres | 210/136 |
| 4,028,056 A | * | 6/1977 | Snyder et al. | 436/514 |

(Continued)

FOREIGN PATENT DOCUMENTS

| | | |
|---|---|---|
| EP | 0419168 B1 | 3/1995 |
| EP | 0512612 B1 | 2/1998 |

(Continued)

OTHER PUBLICATIONS

Tijssen, P., "Practice and Theory of Enzyme ImmunoAssays", Laboratory Techniques in Biochemistry and Molecular Biology, 1985, vol. 15, pp. 297-329, Elsevier Science Publishers.

(Continued)

*Primary Examiner* — John Kim
(74) *Attorney, Agent, or Firm* — The Webb Law Firm

(57) ABSTRACT

The invention relates to a device and method for collecting blood whereby certain target components are isolated or removed from the blood sample at the time of collecting the blood, as well as methods for using such devices.

42 Claims, 15 Drawing Sheets

(56) References Cited

U.S. PATENT DOCUMENTS

| | | | |
|---|---|---|---|
| 4,147,752 A * | 4/1979 | Suovaniemi et al. | 422/429 |
| 4,166,844 A * | 9/1979 | Tu | 436/531 |
| 4,449,539 A | 5/1984 | Sarstedt | |
| 4,697,717 A | 10/1987 | Grippi | |
| 4,837,170 A * | 6/1989 | Ohe et al. | 436/548 |
| 5,024,238 A * | 6/1991 | Guirguis | 435/7.9 |
| 5,264,835 A * | 11/1993 | Shaw et al. | 345/694 |
| 5,306,270 A | 4/1994 | Macartney et al. | |
| 5,342,790 A * | 8/1994 | Levine et al. | 436/523 |
| 5,474,687 A | 12/1995 | Van Vlasselaer | |
| 5,635,362 A * | 6/1997 | Levine et al. | 435/7.24 |
| 5,721,105 A * | 2/1998 | Bergmann | 435/7.1 |
| 5,871,906 A | 2/1999 | Dyer et al. | |
| 6,197,579 B1 * | 3/2001 | Van Vlasselaer et al. | 435/325 |
| 6,242,578 B1 * | 6/2001 | Bogoch et al. | 530/395 |
| 6,368,873 B1 * | 4/2002 | Chang et al. | 436/514 |
| 6,479,298 B1 | 11/2002 | Miller et al. | |
| 6,933,148 B2 * | 8/2005 | Collins et al. | 435/372 |
| 7,067,251 B2 * | 6/2006 | Zauderer et al. | 435/6 |
| 2001/0001708 A1 * | 5/2001 | Antignani et al. | 435/183 |
| 2002/0012906 A1 * | 1/2002 | Comper | 435/4 |

FOREIGN PATENT DOCUMENTS

| | | |
|---|---|---|
| JP | 63-218055 A | 9/1988 |
| JP | 02-088045 | 3/1990 |
| JP | 10-123134 | 5/1998 |
| JP | 10-272124 | 10/1998 |
| JP | 2001-056336 | 2/2001 |
| JP | 2002-116201 | 4/2002 |

OTHER PUBLICATIONS

Worrall, TA et al., "Purification of Contaminated Peptides and Proteins on Synthetic Membrane Surfaces for Matrix-Assisted Laser Desorption/Ionization Mass Spectrometry" Anal. Chem., Feb. 15, 1998, vol. 70, No. 4, pp. 750-756.

* cited by examiner

DEVICES FOR COMPONENT REMOVAL DURING BLOOD COLLECTION, AND USES THEREOF

CROSS REFERENCE TO RELATED APPLICATIONS

This application is a National Stage of International Application No. PCT/US04/02019, filed Feb. 13, 2004, which claims the benefit of U.S. Provisional Application No. 60/447,014, filed Feb. 13, 2003.

BACKGROUND OF THE INVENTION

1. Field of the Invention

The present invention relates to devices and methods for collecting blood whereby certain target components are isolated or removed from the blood sample at the time of collecting the blood, as well as methods of using such devices.

2. Background of the Invention

Today with the growth of proteomics, large-scale isolation and identification of proteins is becoming the focus of research, drug development and diagnostics. Protein separation methods are well-established in the molecular and biochemical arts; however, with the growth of proteomics, new technologies have arisen which require different, more stringent protein separation techniques. For example, exploring the plasma proteome requires the separation and identification of low abundance proteins and the determination of their characteristics using electrophoresis in a 2-dimensional (2D) gel system. However, plasma proteins or other components present in high concentrations, for example albumin, can hinder the separation and obscure the identification of these lower abundance proteins and, at times, make it difficult or impossible to determine their identity on 2D gels or by any other downstream testing of blood samples.

Currently, many different methods exist to remove albumin and other high abundance components from blood samples; however, most of these clean-up methods are not specific enough and may actually remove many of the desirable proteins or components. Current albumin clean-up methods, for example, require transferring the sample into another container, thus requiring additional handling steps, and increasing the risk of processing errors, sample contamination, and extra risk of operator exposure to possibly infectious blood components. Furthermore, current methods do not use any kind of specifically directed affinity molecule targeting the target components in the clean-up process, and may thus remove components of interest. Accordingly, there is a need for blood sample collection devices, methods of using such devices, and processes that eliminate the risk of error and contamination, while also providing specific isolation of target components.

SUMMARY OF THE INVENTION

The present invention relates to a device for collecting blood comprising a reservoir and affinity molecules, wherein the affinity molecules are exposed to blood during the time of blood collection.

The present invention also relates to a method of collecting blood comprising exposing the blood to affinity molecules during the time of blood collection.

DETAILED DESCRIPTION OF THE INVENTION

Figure 1:
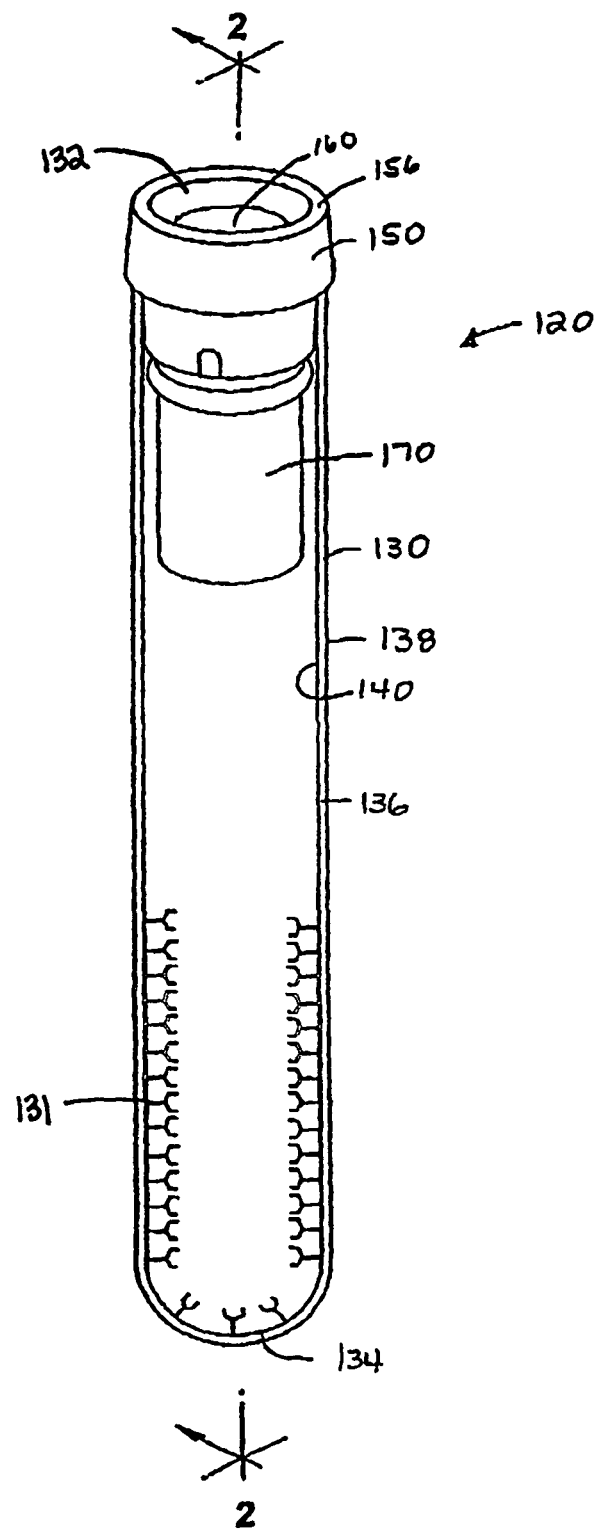
FIG. 1 depicts one of the devices of the present invention.
Figure 2:
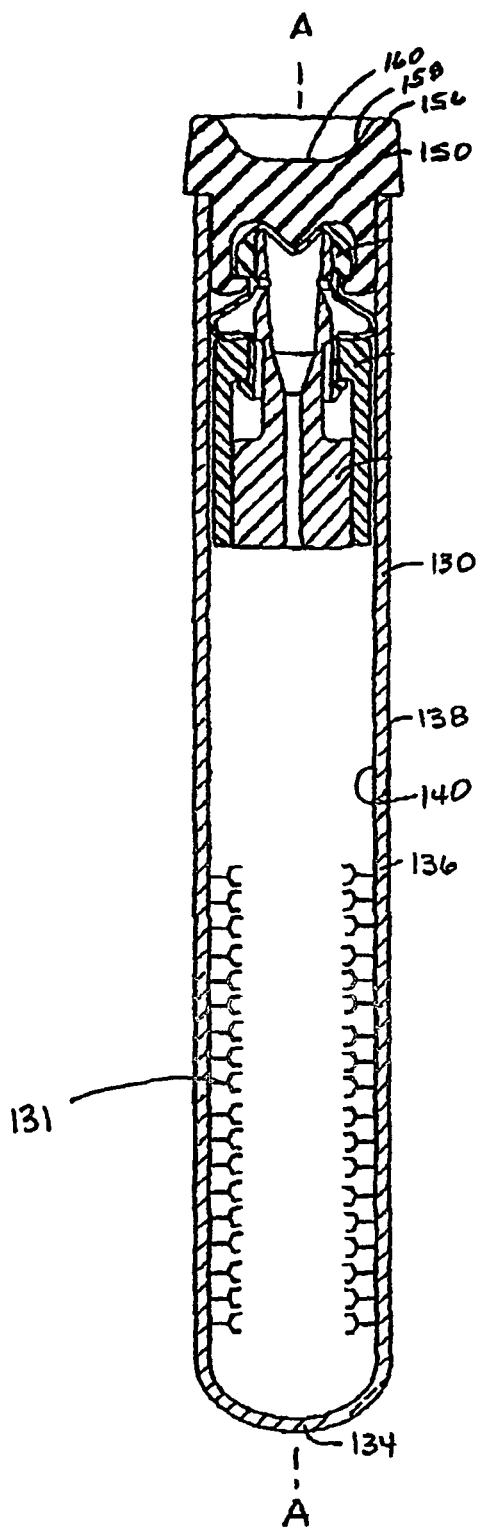
FIG. 2 is a longitudinal sectional view of the device of FIG. 1.

The present invention relates to a device for collecting blood comprising a reservoir and affinity molecules, wherein the affinity molecules are exposed to the blood during the time of collecting the blood.

The present invention also relates to a method of collecting blood comprising exposing the blood to affinity molecules during the time of said collection. The affinity molecules will bind target molecules present in the blood. As used herein, "target molecules" or "targets" is used to mean a component that may or may not be present in the actual sample of blood, but will bind to the affinity molecules if present. The target may be "desired" in that the molecule targeted by the affinity molecule is of interest for further processing or assaying. Alternatively, the target may be "undesired" in that the target may be considered an impurity, or may be unnecessary or unwanted in further processing or assaying steps.

As used herein, "blood" is intended to mean whole blood, or the separate components of whole blood, from any animal. Separate components of blood include, but are not limited to, plasma and serum, the definitions of which are used herein as these terms are used in the art. For example, plasma is the component of whole blood that is substantially free of cells, including platelets. Serum is plasma in which fibrinogen and other clotting factors have been removed. Thus, "blood," as used herein, can include whole blood, plasma, serum, the cellular portion of blood and even the protein portion of whole blood. Furthermore, for the purposes of this invention, components of blood can be isolated, such as the isolation of protein or other molecules from blood such as an isolate of fibrinogen, or can be a mixture of molecules, such as plasma or serum. For example, as used in the current context, albumin is considered a component of blood. As used herein, "component" does not include the cellular portion of blood, whereas, "cellular component" includes cellular portions.

Cellular components may or may not include, and are not limited to, hematopoetic cells, myeloid stem cells, erythrocytes, neutrophils, basophils, eosinophils, megakaryocytes, platelets, monocytes, mast cells, lymphoid cells, including all T-cells and B-cells, normal or diseased cells from any body tissue.

Furthermore, "collecting" is used to mean extraction of the blood from its normal environment, whether or not the blood is returned to the individual from which it was extracted, or placed into a different individual, such as during a transfusion. As used herein, the terms "individual," "subject" and "patient" are used interchangeably and are used to mean any animal, preferably a mammal, more preferably a human or non-human primate.

The device of the present invention comprises a reservoir. The reservoir can be any device, open or closed to the environment, that can hold any amount of blood, at least temporarily. Of course, a reservoir can also hold any amount of blood indefinitely. The reservoir can also be capable of being punctured and resealed. Examples of reservoirs of the current invention include, but are not limited to, evacuated tubes, non-evacuated tubes, petri dishes, microtiter plates, syringe barrels, needles, machines that can process or analyze blood, blood collection systems such as blood collection bags, such as the type used when donating blood, and even plastic tubing.

The blood need not be stationary inside the reservoir, but can be sedentary, or moving or flowing. In one embodiment, the reservoir comprises a density gradient barrier wherein the sample collected within the reservoir is separated into higher and lower densities during centrifugation. Any type of blood collection device or system may be used as a reservoir. Suitable devices and systems that can act as reservoirs include, but are not limited to, blood tubes manufactured by, for example, Becton Dickinson and Company (BD) including, but not limited to, Serum Clot Activator Tubes, Serum Gel Clot Activator Tubes, Lithium Heparin Tubes, Sodium Fluoride Tubes, Sodium Citrate Tubes, ESR Citrate Tubes and Trace Mettal Tubes. Additionally, capillary blood collection systems produced by any manufacturer including, but not limited to, Microvette™ systems can act as reservoirs. Examples of some types of reservoirs contemplated for use in the present invention are contained in U.S. Pat. No. 6,479, 298, the entirety of which is incorporated herein by reference.

In one embodiment, the reservoir further comprises an insert. As used herein, the term "insert" means a material that is completely encapsulated by the reservoir, such as a solid dipstick, mechanical density partition element, or a paddle within an evacuated tube. The term "insert" can also refer to material that is only partially within the reservoir. The inserts can be a solid object, such as a paddle, or the inserts can be a liquid, a gel or a gas. Other examples of inserts include, but are not limited to, beads, particles and microparticles. Examples of beads include, but are not limited to, paramagnetic beads that can be manipulated by a magnetic field. The inserts can be any shape, provided that at least a portion of the insert is located within the reservoir. Examples of the shapes of inserts include, but are not limited to, rectangular, circular, oval, straight rod and helical-shaped rod.

In another embodiment, the interior walls of the reservoir can be smooth or ridged. Providing a reservoir with ridges serves to increase the interior surface area of the reservoir. In yet another embodiment, the inserts are also ridged to increase their respective surface areas. In still another embodiment, both the insert and the interior walls of the reservoir are ridged to provide even more surface area. The purpose of increasing the surface area in any of the embodiments of the present invention is to increase the amount of surface-immobilized affinity molecules that can come into contact with the blood at the time of its collection.

In addition to the reservoir, the device of the present invention also comprises one or more affinity molecules. As used herein, "affinity molecules" can be any type of molecule that possesses an affinity towards single or multiple components of the blood. The affinity can be a specific affinity in that the affinity molecule has an affinity for a focused subset of components, such as an antibody specific for fibrinogen. The affinity of the affinity molecules can also be less specific in nature, such as a protein that binds the general class immunoglobulins, for example, protein A. Even further, the affinity molecules as contemplated by the present invention can exhibit an even broader affinity such that the affinity molecules can possess an affinity for a mixture of different classes of proteins.

Examples of affinity molecules include, but are not limited to, antibodies, antibody fragments, enzymes, fragments of enzymes, enzyme substrates, fragments of enzyme substrates, nucleotides, oligonucleotides, polynucleotides, receptors, fragments of receptors, ligands, fragments of enzymes, other proteins, amino acids, peptides, polypeptides, oligopeptides, saccharides, disaccharides, polysaccharides, glycoproteins, proteoglycans, natural and synthetic polymers, aptamers, and nanobodies. In one embodiment, the affinity molecules are antibodies, or fragments of antibodies, such as, but not limited to, Fab fragments, $F(ab')_2$ fragments, and scFv fragments. The antibodies may be polyclonal, monoclonal, chimeric, synthetic or naturally occurring.

In another embodiment, the affinity molecules of the present invention bind a component within the blood. Preferably, the affinity molecules bind a blood protein. Examples of proteins that the affinity molecules will bind include, but are not limited to, fibrinogen, albumin, immunoglobulins including, but not limited to, alpha-, beta- and gamma-globulins, proteases such as chymotrypsin and thrombin, and protease inhibitors such as antichymotrypsin, antithrombin, macroglobulins, inter-alpha-trypsin inhibitor, C1 inhibitor, plasmin inhibitor, heparin cofactor II, apoprotein A and fibronectin.

In one embodiment, the affinity molecule or set of affinity molecules can bind to more than one undesired component at the same time, resulting in more than one undesired component being removed from the sample. In another embodiment, the affinity molecule or set of affinity molecules can bind to more than one desired component at the same time, resulting in more than one desired component being isolated. In another embodiment, more than one affinity molecule or set of affinity molecules can be employed, with each affinity molecule or set of molecules binding different undesired components, resulting in more than one undesired component being removed from the sample. Of course, the invention encompasses utilizing one affinity molecule or set of affinity molecules that can bind only one undesired component. Optionally, the invention encompasses utilizing one affinity molecule or a set of affinity molecules that can enrich the sample by removing all but a few desired components from the original specimen. As used herein, the phrase "a set of affinity molecules" is used to mean a plurality of affinity molecules that possess the identical type of affinity, in both specificity and strength. As used herein, "affinity molecules" is used to mean one or more affinity molecules and one or more sets of affinity molecules. In one embodiment, the invention encompasses a reservoir and a single device, comprising an affinity molecule or a set of affinity molecules. In another embodiment, the invention also encompasses a single device, comprising a mixture of more than one distinct affinity molecules or sets of molecules. In yet another example, the invention also comprises multiple devices, with each device comprising a distinct affinity molecule or set of affinity molecules directed towards, for example, immunoglobulins and clotting factors. In still another embodiment, the invention also comprises multiple devices, with each device comprising a mixture of more than one distinct affinity molecules or sets of affinity molecules. In still another embodiment, the invention also comprises a kit of multiple devices, with each device comprising a mixture of more than one distinct affinity molecules or sets of affinity molecules.

The affinity molecules of the present invention can be present in soluble or immobilized form. If, for example, the affinity molecules are in soluble form, they may be present in the reservoir in liquid or lyophilized form. The blood would then be added to the solubilized affinity molecules, which could then be pulled out of the sample or fractionated from the sample depending on the specific user needs for the final sample. For example, the affinity molecules can be bound or attached to inert substances such as, for example, glass, polypropylene, nylon, nitrocellulose, polymethacrylate, polystyrene, polyvinylchloride, styrenebutadiene copolymer, styrene-acrylate copolymer, latex, chemically modified plastic, rubber, red blood cells, a polymeric material or biological cells. According to the present invention, examples of the surfaces on which the inert substances can be found include, but are not limited to, any portion of the reservoir, the sides and/or bottoms of tubes, the sides and/or bottom of culture dishes, any type of insert such as a paddle, dipstick, gel, beads, particles, microparticles, and the lining of tubing. The affinity molecules can be attached to the surfaces by any known method including, but not limited to, covalent and non-covalent attachment or coupling, such as attaching the affinity molecules directly to the inert surfaces or attaching the affinity molecules to derivatized and/or coated surfaces.

In one embodiment, microparticles such as beads are used in the present invention, with the beads comprising sepharose or polystyrene. In another embodiment, the beads may comprise magnetic particles, such as magnetic, paramagnetic, and superparamagnetic beads produced by Dynal AS (Oslo, Norway) and sold as DYNABEADS™. If magnetic beads are used, regardless of the manufacturer, a magnet could be used to manipulate the movement of the proteins bound to the beads. The magnet can further be used to collect or separate the beads from the rest of the blood sample.

In another embodiment of the present of the invention, a density separator gradient may be introduced to further separate density phases of a collected sample. Such density gradients may be chosen from the group consisting of a thixotropic gel and a mechanical separator. Additionally, beads or microparticles may be chosen such that their density is greater than the density separator. For instance, if the density of the separator is about 1.02 to about 1.08 $g/cm^3$, the density of the beads may be chosen such that all or a portion of the beads have a density greater than about 1.08 $g/cm^3$. The higher density beads should come to rest at the bottom of the container during centrifugation, thus moving a portion of the bound targets below the density separator. When the targeted molecules are highly abundant, removal of the beads or microparticles will thus enrich the sample remaining in the reservoir. In another embodiment of the present invention, beads may be chosen such that their density is smaller than the density of a density separator. For instance, if the density of the separator is about 1.02 to about 1.08 $g/cm^3$, the density of the beads may be chosen such that all or a portion of the beads have a density lower than about 1.02 $g/cm^3$. The lower density beads should float to the top of the sample, thus moving a portion of the bound targeted proteins above the separator. When the targeted molecules are highly abundant, removal of the beads or microparticles will thus enrich the sample remaining in the reservoir.

The thixotropic gel separator may be applied to the inner surface the reservoir. Alternately, a mechanical separator may be inserted within the tube to separate fluids. Once the blood collection tube is subjected to centrifugal force, the separator will then move up or down the tube as it comes into a density equilibrium with the blood sample, thus acting to set up a density gradient for the blood. In conjunction with the separator, the beads, if used in the present invention, can also act within and help establish a density gradient to allow ease of separation of the various components of the blood.

The present invention may be embodied in other specific forms and is not limited to any specific embodiments described in detail, which are merely exemplary. Various other modifications will be apparent to and readily made by those skilled in the art without departing from the scope and spirit of the invention. The scope of the invention will be measured by the appended claims and their equivalents.

One embodiment of the present invention is illustrated in FIGS. 1-6, wherein assembly 120 comprises a reservoir 130 (here, depicted as a tube), a closure 150 and a separator 170.

Reservoir 130 has an open end 132 that includes a top edge (not shown), a closed end 134 and a sidewall 136 extending between the open end and the closed end. Sidewall 136 has an outer surface 138 and an inner surface 140. Reservoir 130 defines a receptacle with a central axis "A". Assembly 120 includes affinity molecules 131 located on inner surface 140 of sidewall 136.

Closure 150 is disposed to fit over open end 132 of reservoir 130. Closure 150 comprises an annular upper portion 152, which extends over the top edge of sidewall 136, and a lower annular portion or skirt 154 of lesser diameter than the annular upper portion 152, which extends into and forms an interference fit with inner surface 140 of sidewall 136 for maintaining closure 150 in place in open end 132.

Annular upper portion 152 includes a top surface area 156, sidewall 158 that converges from surface area 156 towards upper well area 160. Lower annular skirt portion 154 defines a lower well 162, an inner wall surface 164, an outer wall surface 166 and a bottom surface 168. Well area 160 and lower well area 162 define a thin diaphragm or self-sealing septum through which a needle may be inserted. The self-sealing septum material allows penetration by a piercing element such as a needle and then reseals when the piercing element is withdrawn.

An annular ledge or abutment 157 separates annular upper portion 152 and lower annular portion 154.

Preferably, closure 150 is made of natural rubber elastomer, synthetic thermoplastic and thermoset elastomeric materials. Preferably, the closure is made of a resilient elastomeric material whereby the septum is self-sealing.

Figure 3:
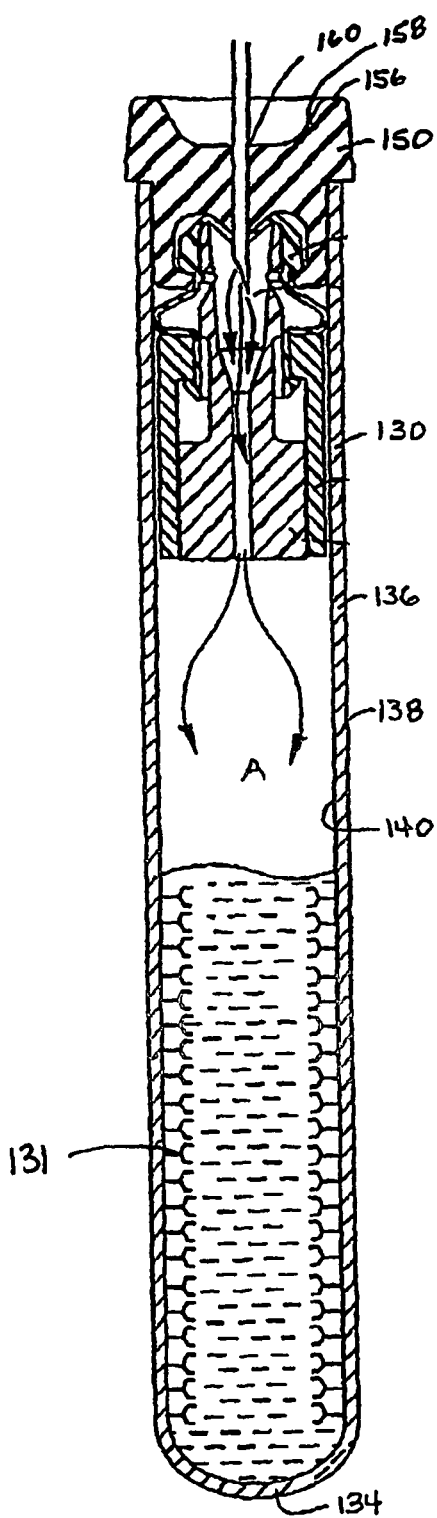
FIG. 3 is a longitudinal sectional view of the device of FIG. 1, illustrating fluid delivery into the device.

As shown in FIG. 3, a liquid sample A is delivered to the tube by a needle that penetrates closure 150 in upper well area 160. For purposes of illustration only, the liquid sample is blood. The liquid sample is delivered into the passageway of separator 170 so that the liquid sample is introduced between closed end 134 of reservoir 130 and separator 170, whereby the outer surface of all components of separator 170 are substantially free of any contact with the fluid sample.

Figure 4:
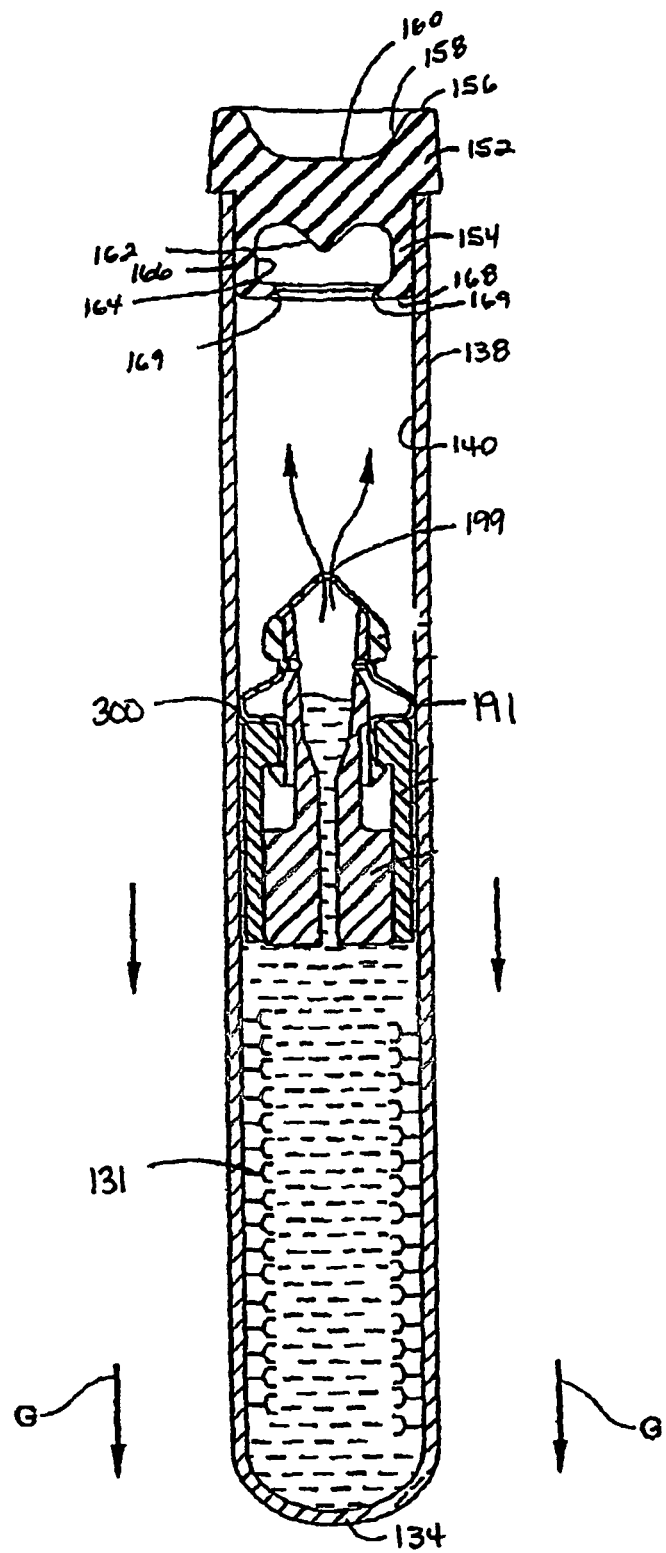
FIG. 4 illustrates the device of FIG. 1 during centrifugation, with the subsequent release of the separator.
Figure 5:
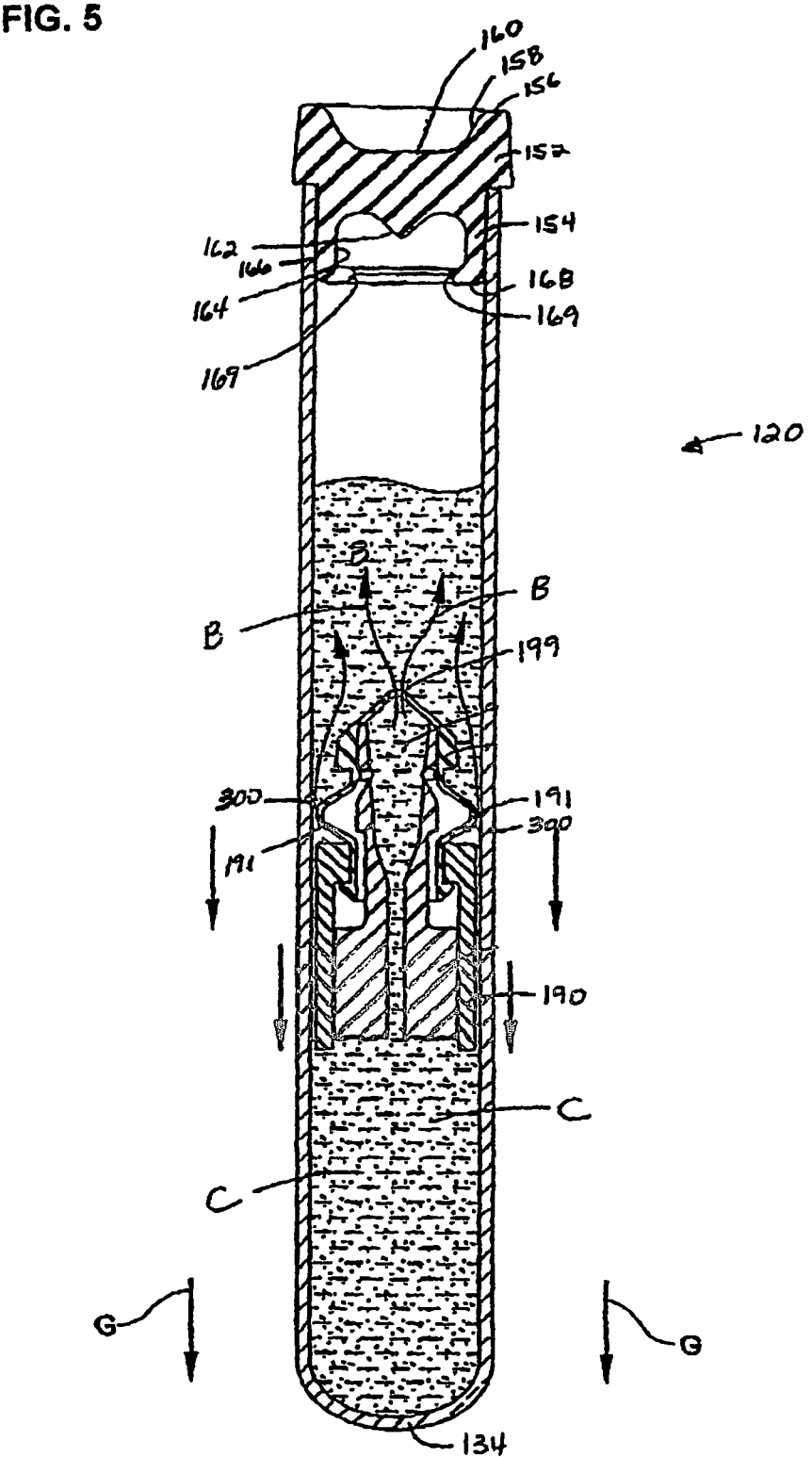
FIG. 5 also illustrates the device of FIG. 1 during centrifugation, with the subsequent release of the separator.

As shown in FIGS. 4 and 5, when assembly 120 is subjected to centrifugation or axial centrifugation force, seal body 191 of separator 170 deflects, thereby reducing its diameter and eliminating its interference fit with the inner wall of the reservoir. Separator 170 releases from the inner wall of the reservoir such that separator 170 descends towards closed end 134 of reservoir 130. This also opens up a path 300 between the reservoir and the separator, permitting the flow of the low-density component B of the fluid upwardly past the separator as the separator migrates down the reservoir. The low-density component inside the passageway 199 of the separator will migrate downwardly and upwardly past the separator. Thus, separator 170 is permitted to sink into the fluid sample.

Figure 6:
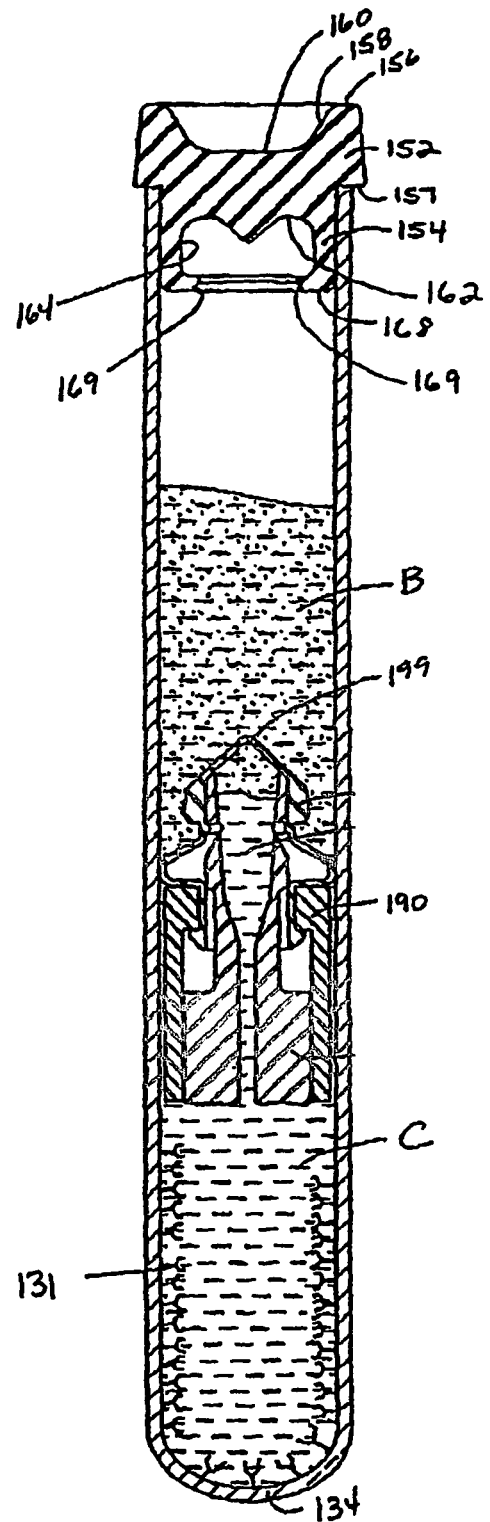
FIG. 6 illustrates the device of FIG. 1 after centrifugation, showing the separation of the liquid sample into higher and lower specific gravities.
Figure 7:
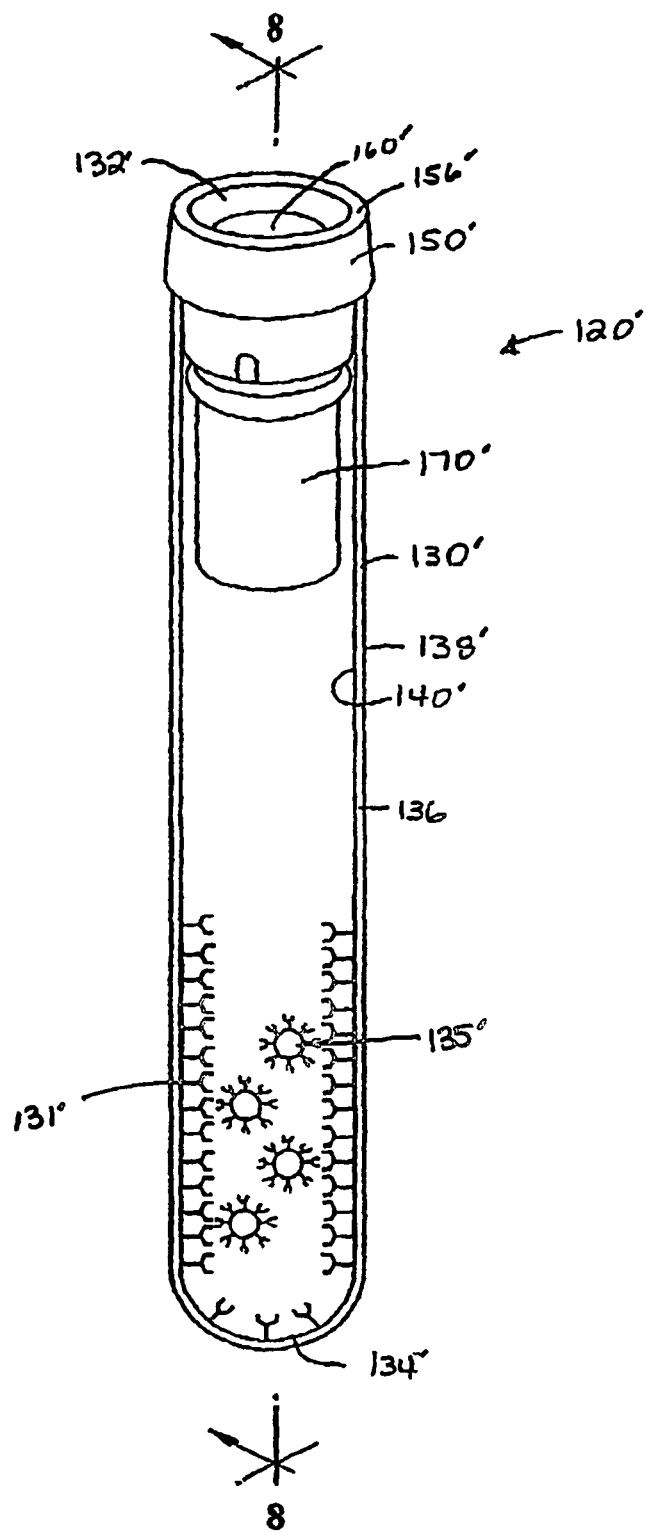
FIG. 7 depicts another device of the present invention.
Figure 8:
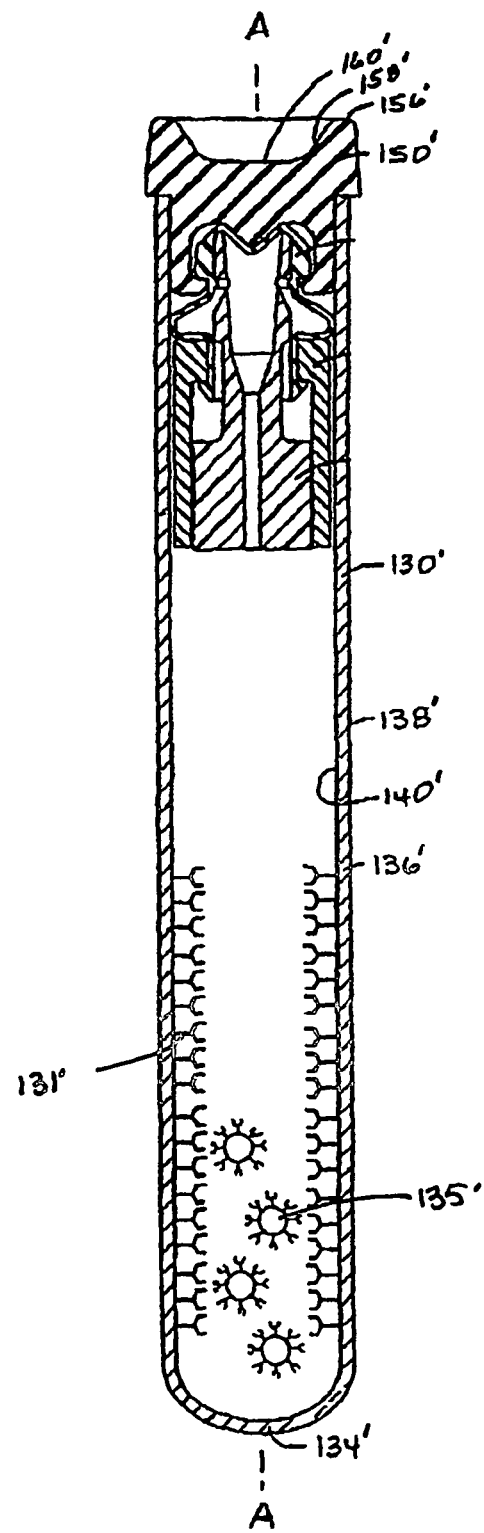
FIG. 8 is a longitudinal sectional view of the device of FIG. 7.
Figure 9:
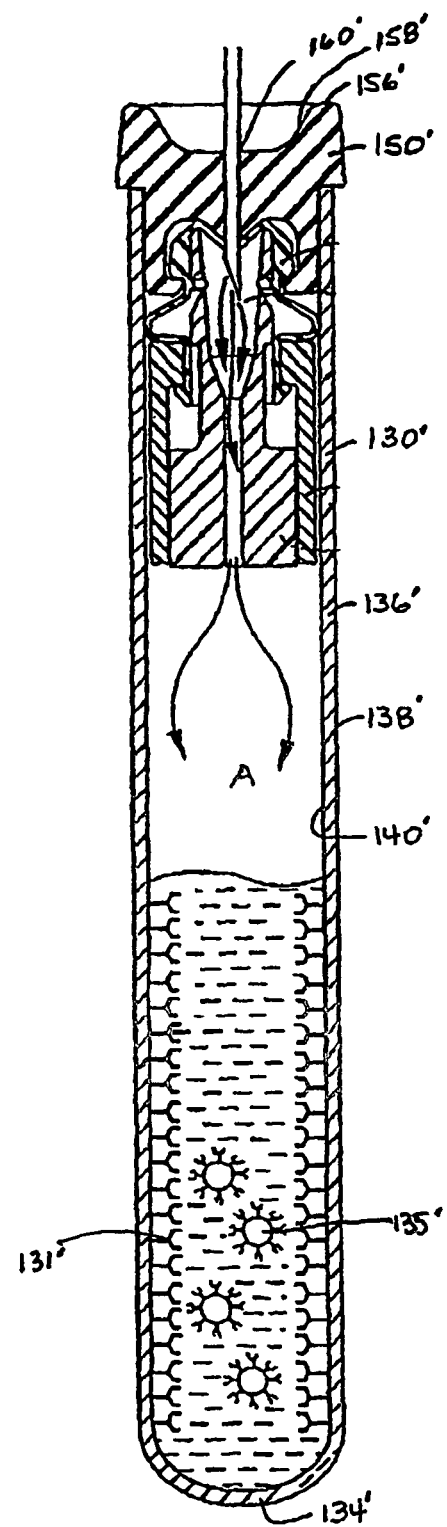
FIG. 9 is a longitudinal sectional view of the device of FIG. 7, illustrating fluid delivery into the device.
Figure 10:
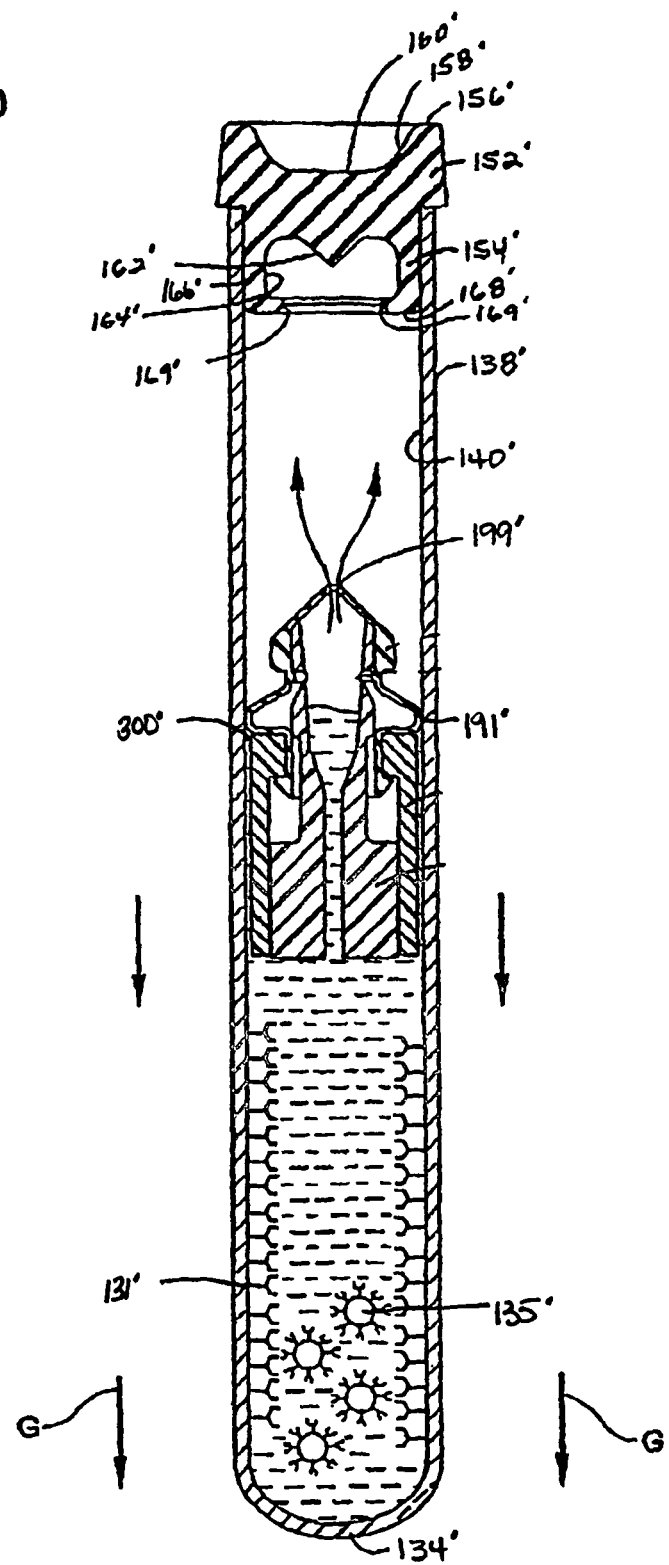
FIG. 10 illustrates the device of FIG. 7 during centrifugation, with subsequent release of the separator.
Figure 11:
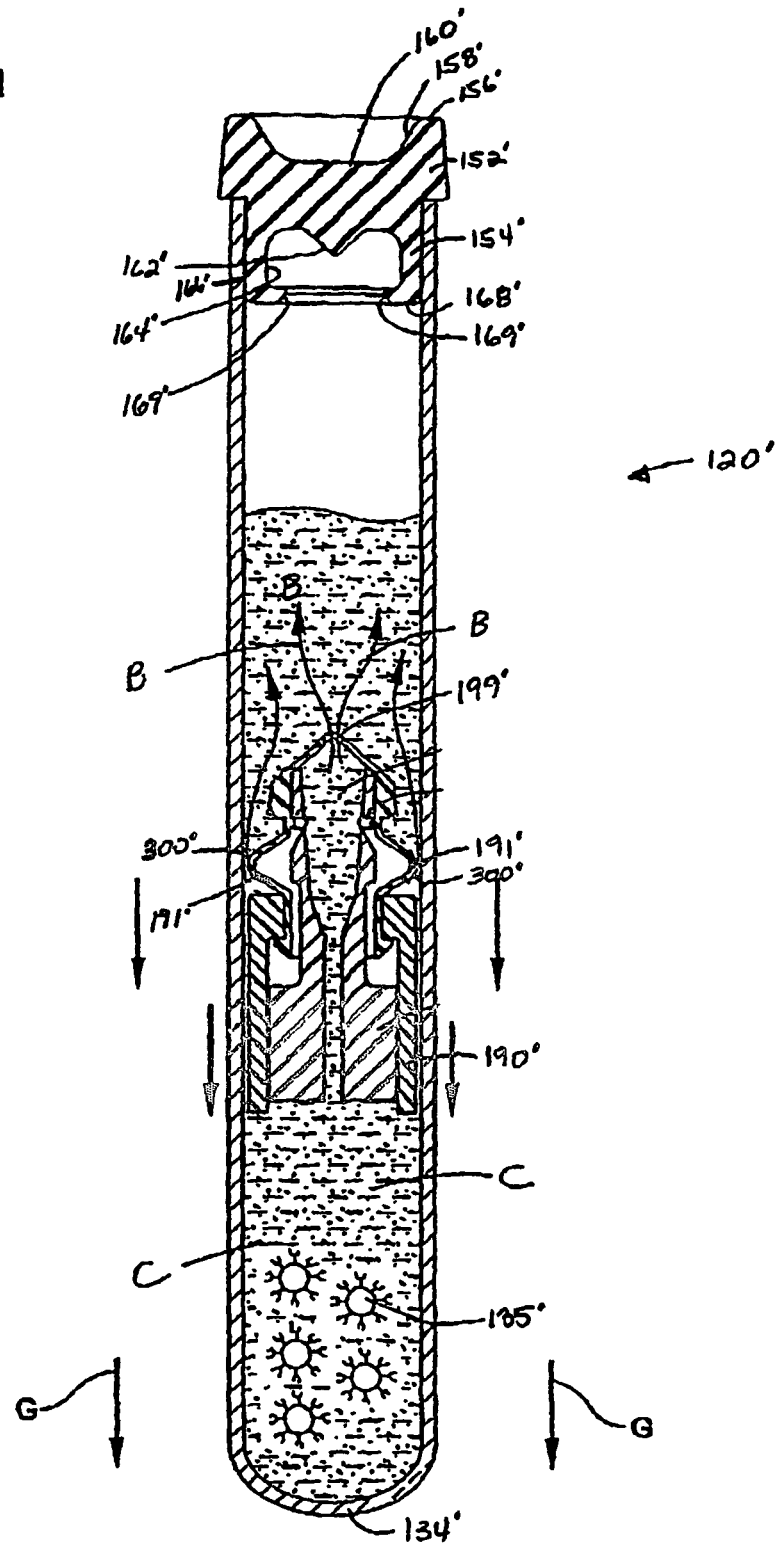
FIG. 11 also illustrates the device of FIG. 7 during centrifugation, with subsequent release of the separator.
Figure 12:
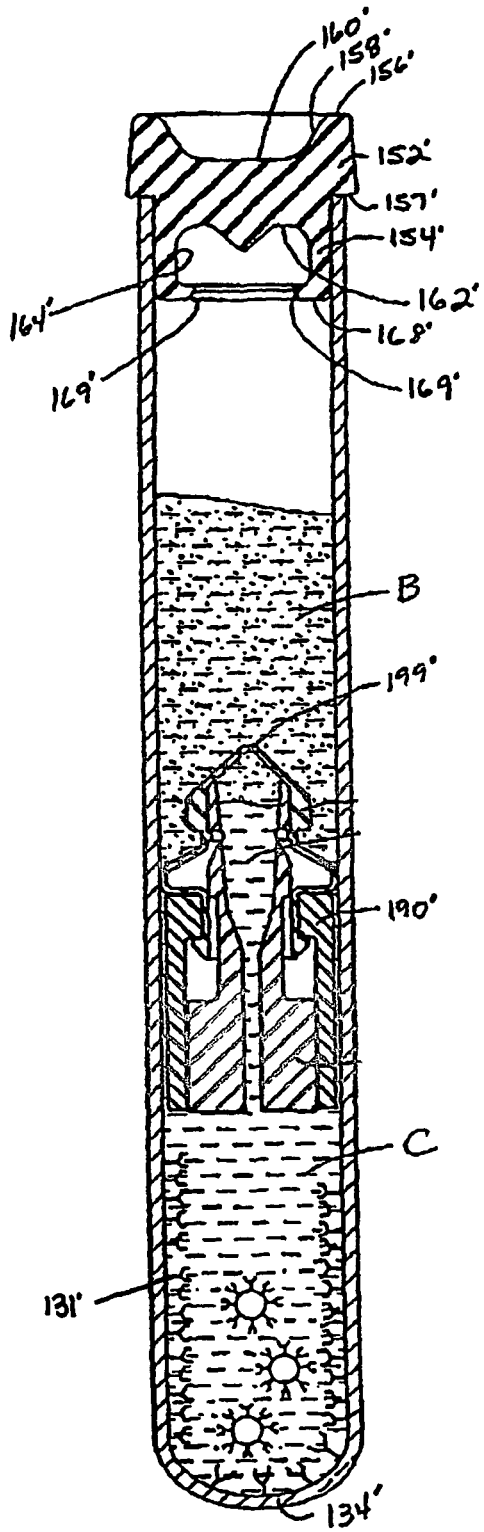
FIG. 12 illustrates the device of FIG. 7 after centrifugation, showing separation of the liquid sample into higher and lower specific gravities.

As shown in FIG. 6, after centrifugation is terminated, the absence of the centrifugal load will cause seal body 191 to resiliently return toward an underformed condition and tightly seal with the inner wall of the tube. Thus, separator 170 serves as a divider between lower specific gravity portion B and higher specific gravity portion C of the liquid sample.

FIGS. 7-12 represent an alternative embodiment of the present invention. The embodiment of FIGS. 7-12 operates in the same manner as the embodiment of FIGS. 1-6, but contains beads 135' with affinity molecules 131' thereon, as well as affinity molecules 131' located on inner surface 140' of sidewall 136'. Elements common to the embodiment of FIGS. 1-6 and FIGS. 7-12 are numbered identically, with those of the latter embodiment denoted as "prime" (').

Figure 13:
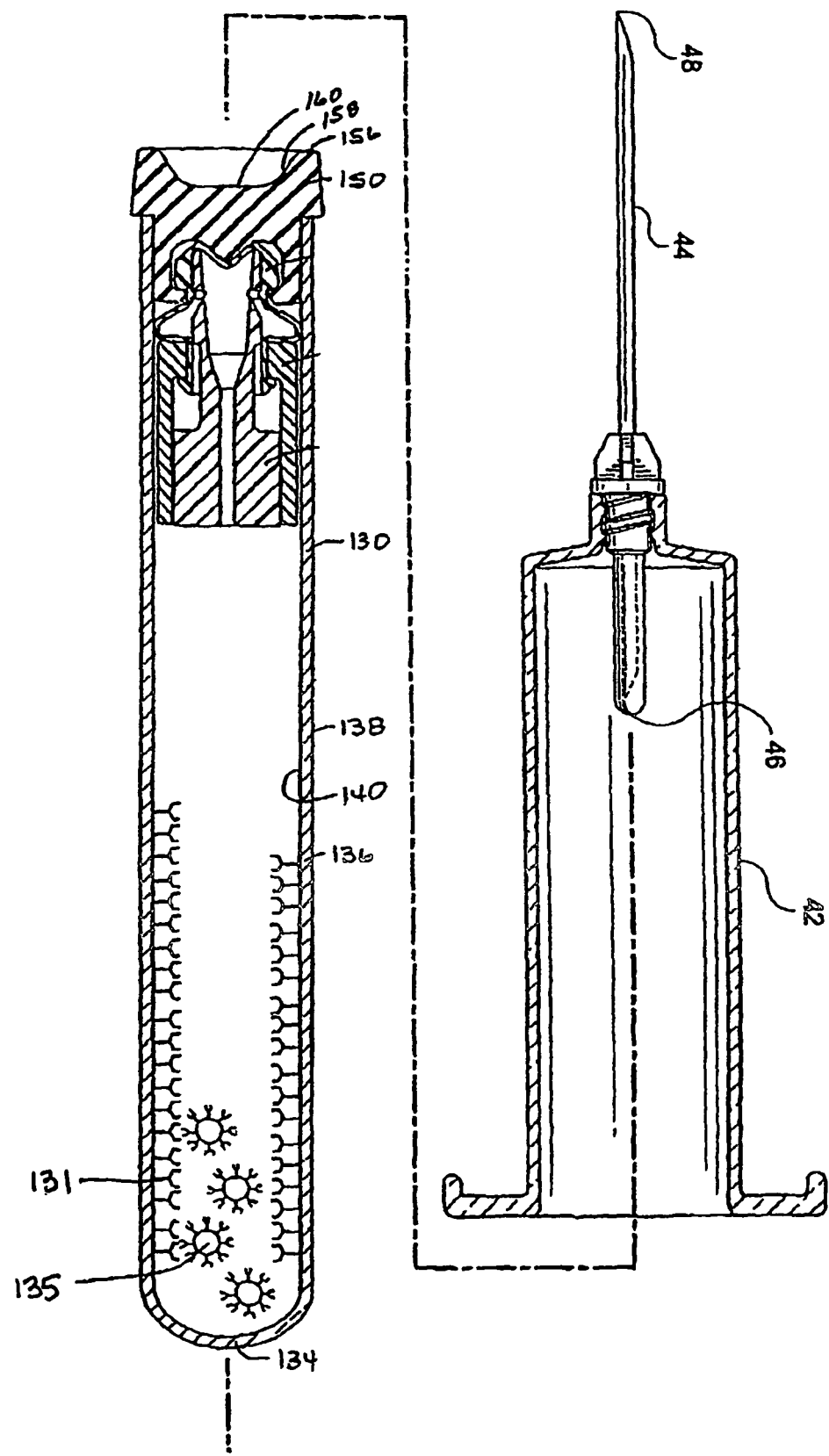
FIG. 13 depicts another device of the present invention.

FIG. 13 shows the interaction of the device of FIGS. 1-6 with a holder 42. Holder 42 has a cannula 44 with a venous entry end 48 and a non-patient end 46 such that when assembly 120 is inserted into holder 42, the self-sealing septum on closure 150 is pierced by non-patient end 46, thereby starting the process of collecting blood into reservoir 130.

In one embodiment, the reservoir is compatible with the numerous additives used in the art such as citrates, silicone, silicates, ethylenediaminetetraacetic acid (EDTA) and the like. The additives are used, for example, to condition the sample either to facilitate or retard clotting or to preserve the sample for a particular analysis. It is within the purview of the present invention that one or more additives may be used.

The affinity molecules themselves may or may not be modified to allow ease of separation. For example, the affinity molecules may be biotinylated, and streptavidin could be used to remove the biotinylated affinity molecules after having bound the target component. Thus, a component can be removed from a sample first by exposing the affinity molecules to the sample at the time of collection and subsequently using biotinylated anti-affinity molecule antibodies. The biotinylated antibodies would then be captured using, for example, avidin, streptavidin, or Neutravidin™, resulting in a sample substantially depleted of the targeted component.

In one embodiment, the affinity molecules are found within the reservoir. For example, the affinity molecules may be bound to beads, which are found within the reservoir. Thus, the invention can comprise an evacuated blood collection device with, for example, antibody-coated beads added to the tube. The tube containing the beads would be used, for example, during venipuncture blood collection procedures in humans and/or animals. In a similar embodiment, the invention could also be, for example, non-evacuated micro-collection containers containing antibody-coated beads. The foregoing embodiment can be modified, for example, by substituting the beads for any inert substance or surface, whether or not the inert substance or surface is listed herein.

In another embodiment, the affinity molecules may be external to the reservoir. For example, the affinity molecules may be bound to beads that are external to the reservoir and may comprise, for example, an affinity column packed with affinity beads. Thus, the invention can also comprise a reservoir for collecting the blood and one or more affinity columns linked, in sequence, before or after and optionally integrated to the reservoir. The foregoing embodiment can be modified, for example, by substituting the beads for any portion of the reservoir, the sides and/or bottoms of tubes, particles, microparticles, the sides and/or bottom of culture dishes and the lining of tubing.

Indeed, the foregoing embodiments can be modified, for example, by substituting the beads for any inert substance or surface, whether or not the inert substance or surface is listed herein. Further, all of the embodiments described herein can also be modified by substituting antibodies, for example, with any type of affinity molecule such as antibody fragments, enzymes, fragments of enzymes, enzyme substrates, fragments of enzyme substrates, nucleotides, oligonucleotides, polynucleotides, receptors, fragments of receptors, ligands, fragments of enzymes, other proteins, amino acids, peptides, polypeptides, oligopeptides, saccharides, disaccharides, polysaccharides, glycoproteins, proteoglycans, and natural and synthetic polymers. Further, all of the embodiments described herein can be modified by substituting protein for any undesirable component of blood.

The present invention provides distinct advantages over current methods, these advantages being achieved by exposing the affinity molecules to the blood during and/or immediately after the blood collection process. As used herein, "during the time of collection" is used to mean that the affinity molecules are exposed to the blood during the blood collection process. The exposure of the blood to the affinity molecules need not be brief or instantaneous in time, so long as the exposure of the blood to the affinity molecules occurs prior to any subsequent processing or analysis of the blood sample. Thus, the affinity molecules must be situated in such a manner as to come into contact with the blood during the time of collection. As such, the affinity molecules may be situated to where they come into contact with the blood either before or after the blood collects in the reservoir, so long as the affinity molecules contact the blood during the time of collection. The purpose of contacting the affinity molecules with the blood during the time of collection is to reduce the number of handling and processing steps.

Therefore, present invention provides a means of separating abundant proteins or other components from blood by adding, for example, polystyrene microparticles coated with antibodies specific to blood proteins or other components. The microparticles, for example, can be readily purchased from the manufacturer of microspheres and are designed for immunological applications. Such microspheres are sold with antibodies, without antibodies, or are derivative-ready for antibody conjugation.

The methods of the present invention can serve as an integrated and self-contained one-step clean-up tool or, alternatively, an integrated and self-contained one-step enrichment tool, for downstream testing during the blood collection process. Accordingly, the collection and removal of at least one undesired component from the blood sample can be performed during the same procedure. After clot formation in serum (or no clot formation in plasma), the sample can optionally be subjected to a short waiting period for the binding reaction to take place to the coated polystyrene beads, for example. The time required for the reaction will depend on the kinetics associated with the binding for the intended targets and may be affected by other factors such as, but not limited to, diffusion or mixing.

After exposure of the blood to the affinity molecules, the sample can then be centrifuged, for example, according to the manufacturer's recommendations, allowing the particles with the bound undesired component to settle out at the same rate or faster than the clot or other cellular portion of the blood. The affinity molecule-coated particles, for example, should be of similar density as the clot or the cells so that all of the bound components will settle out of the serum or the plasma. Alternatively, the density and size can be chosen so that the bound components will float. Particles coated with affinity molecules can be chosen based, on specific sizes and densities. Accordingly, the methods of the present invention can remove most or all of the targeted components of the blood, based on the time of incubation, before centrifugation. The removal need not be complete such that 100% of the undesired component is removed from the blood. Rather, all that is required is that the removal of at least one component of the blood be to such a degree that will allow more accurate analysis and/or efficient processing of the blood, compared to blood where the undesired component has not been removed. The resulting plasma or serum, for example, should be sufficiently free of undesired components, and most other components should not be affected because of the specificity of the affinity molecules toward the specific components.

In another embodiment, for example, tube walls can be coated with affinity molecules. In this case, the tube walls would function as a solid support, and the affinity molecules would be conjugated, covalently or noncovalently, to the polymers or particles of the tube. The targeted components would attach to the tube wall and remain there during any pre-analytic steps. Accordingly, samples would be enriched during the collection process and, after centrifugation, the enriched samples could be used directly from the primary tube or transferred to a secondary container.

Figure 14:
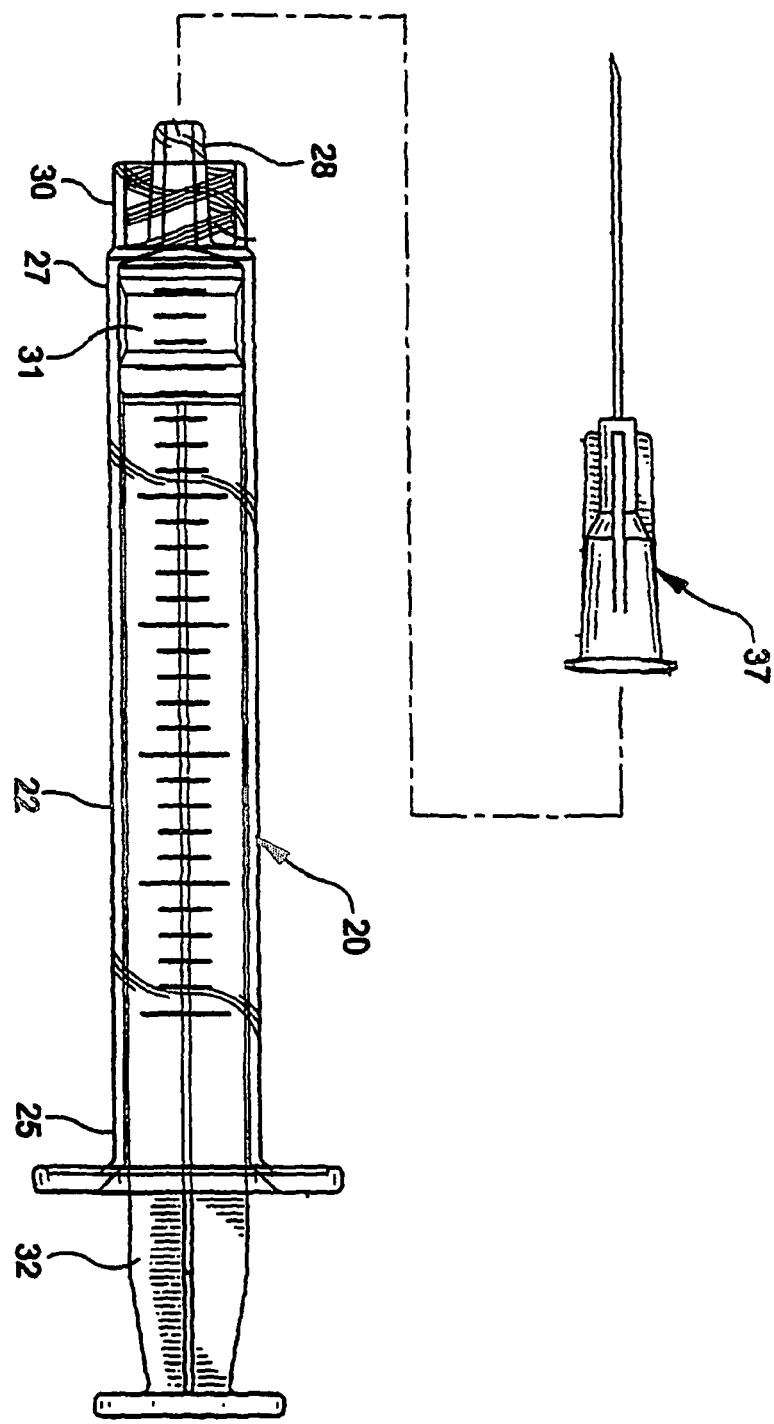
FIG. 14 depicts another device of the present invention, wherein antibody-coated beads are placed within a syringe assembly.

In another embodiment, as depicted in FIG. 14, the reservoir can be formed by a syringe barrel and stopper assembly. The syringe 20 would comprise syringe body 22 having distal end 27 and proximal end 25, a stopper 31 axially movable within the syringe body, and a distal end 30 for mating with a needle assembly 37. The distal end for mating with a needle assembly could, in one embodiment, comprise a frusto-conical tapered male luer 28, thereby providing a conduit from the reservoir to and through the distal male luer taper. Typically, a hypodermic needle comprising a female luer hub with a distally extending lumen forming a conduit from the female luer to the distal lumen tip, would be employed onto the frusto-conical tapered male luer on the distal end of the syringe body.

In other embodiments, the distal end for mating with a needle assembly could comprise an elastomeric access seal so that a cannula integral with a needle assembly can puncture the elastomeric access seal thus establishing fluid communication with the reservoir. The needle assembly would comprise both an elastomeric seal puncture cannula and a venous access cannula such as a stainless steel needle. Specifically, the elastomeric seal puncture cannula would pierce through the elastomeric access seal to establish fluid communication between the reservoir and a patient's vein. In certain embodiments, the needle assembly would have hook elements to reversibly mate to lugs radially extending from the distal portion of the syringe barrel. Examples of such devices are found, for example, in U.S. Pat. No. 4,449,539, the disclosure of which is hereby incorporated by reference.

Syringe body 22 houses an axially movable stopper 31, as known in the art. Preferably, a plunger rod 32 integral to stopper 31 extends proximally from stopper 31 and can be manipulated by a user to move stopper 31 along the axis of syringe body 22. Movement of the stopper causes compression or expansion of the reservoir. According to the present invention, affinity molecules (not shown) are positioned inside the reservoir. In certain embodiments, the affinity molecules are placed on the inner sidewalls of the syringe body. In other embodiments, the affinity molecules are attached to one or more inserts disposed within the reservoir of the syringe assembly. It is possible to provide an initial space between the stopper and the distal end of the syringe body to provide space for such inserts to be present prior to collection. In further embodiments, affinity molecules are placed on the one or more inserts and on the inner sidewalls of the syringe. Preferably, the inserts would include microparticles or beads. In some embodiments, the inserts would be small enough to be able to exit the reservoir without disassembling the assembly such as exiting the lumen extending through the male luer taper or the lumen of the cannula puncturing the elastomeric seal described above. In other embodiments, the inserts would be large enough to be retained within the reservoir, or a mesh or filter can be provided to prevent exit of smaller inserts such as microparticles. In further embodiments, a combination of inserts large enough to be retained within the reservoir and small enough to be able to exit the reservoir delimited by the syringe barrel and stopper may be present. In the embodiments described above, the inserts can be comprised of particles that do and do not respond to magnetic fields placed near the syringe barrel assembly.

Figure 15:
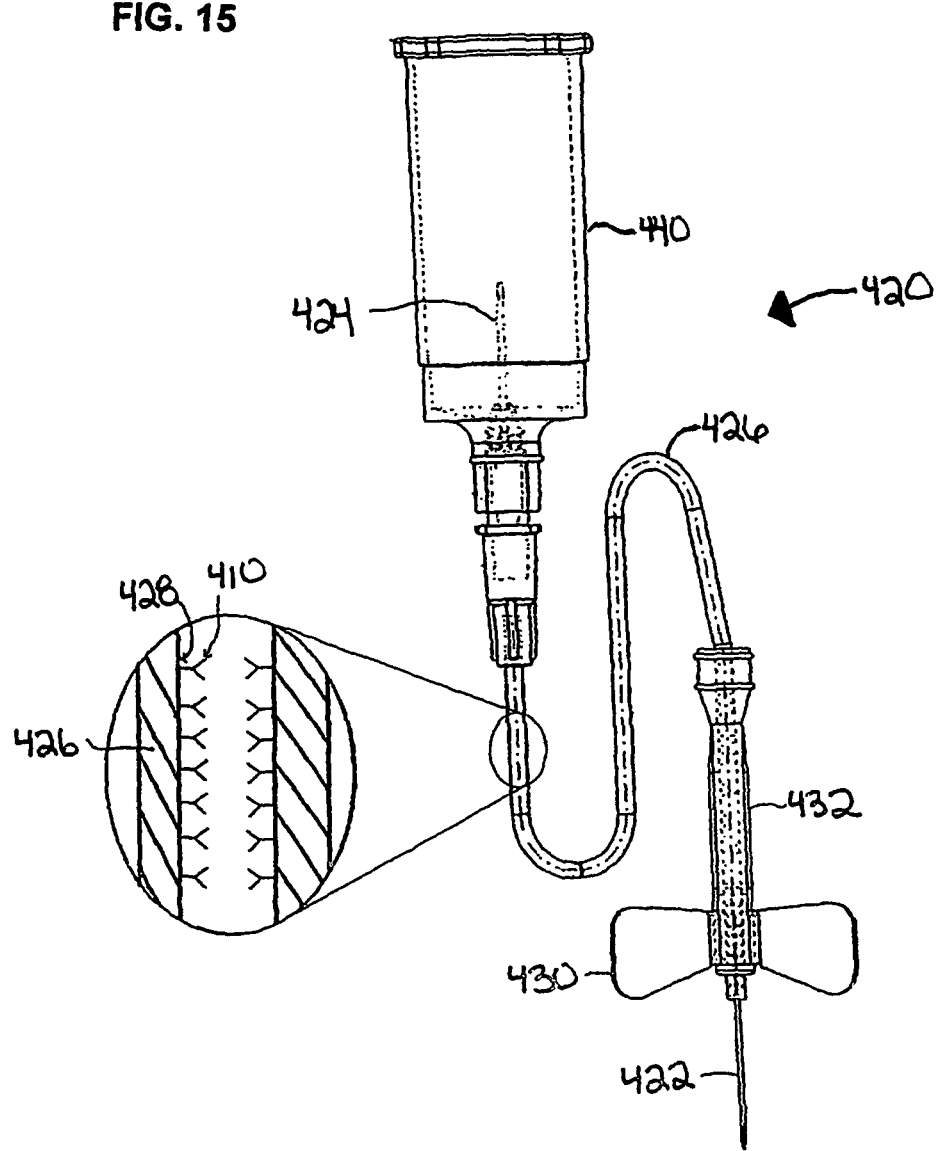
FIG. 15 depicts another device of the present invention, wherein antibody-coated tubing is used for in-line component removal.

Illustrated in FIG. 15 is another embodiment of the present invention in which the affinity molecules 410 are placed in a conduit 426 that communicates between a collection vessel and a venous access element. The venous access element may include catheters, blood collection sets, dialysis needle sets, fluid administration sets, hemodialysis needle sets, aphaeresis needles, blood bags attached to tubing with port access elements or skin puncture needles, and the like. In some embodiments, the venous access point can directly access a vein through a purcutaneous puncture or indirectly by accessing a port that is in fluid communication with a vein. The conduit is preferably a flexible section of polymer tubing such as PVC. Affinity molecules can be disposed inside the conduit directly by adherence to the conduit's inner sidewall surface 428. Alternately, affinity molecules can be disposed inside the conduit by disposing inserts such as beads or microparticles inside the conduit. The size and shape of the inserts can be such that they are maintained inside the conduit and are restricted from traveling freely within the conduit because of size restrictions or other elements added to retain their location.

FIG. 15 shows a blood collection set 420 with an intravenous puncture needle 422, a reservoir access needle 424, and a conduit 426, which contains affinity molecules 410, extending therebetween. Integrated to intravenous puncture needle 422 is a wing element 430 extending laterally on both sides of the intravenous puncture needle. The wing element also establishes a hub 432 that helps interface conduit 426 to the inner lumen of intravenous puncture needle 422. Conduit 426 can directly or indirectly interface with reservoir access needle 424. Indirectly, conduit 426 can be integral with a female luered connector that is further integrated to a male luer hub bonded to the reservoir access needle. Preferably, surrounding reservoir access needle 424 would be a collection container holder 440 that facilitates the connection of a blood collection tube or blood culture bottle to blood collection set 420. Additionally, a shield element may be disposed on or about the distal portion of the conduit to provide shielding of the distal tip of the intravenous access needle. In additional embodiments, the intravenous puncture needle can be replaced by a valve such as a luer-activated valve. Examples of luer activated valves include the Alarais SmartSite® Needle-less valve sold by Alaris Medical Systems and the Clave® valve sold by ICU Medical. Alternatively, the intravenous puncture needle can be replaced by a stop-cock port or possibly a split septum port such as the Interlink® system sold by Baxter International, Inc.

EXAMPLES

Example 1

Coating Evacuated Polystyrene Tubes with High Affinity Antibodies

High affinity antibodies (~$10^{-8}$ M-~$10^{-12}$ M) directed toward, for example, albumin ("albumin antibodies") can be purchased from various suppliers. Polystyrene tubes are sterilized, and the albumin antibodies are covalently linked to the tubes as outlined in Tijssen, P., Practice and Theory of Enzyme ImmunoAssays, in Burdon, R H and Knippenberg, P H, (Eds.), *Laboratory Techniques in Biochemistry and Molecular Biology*, Elsevier Science Publishers, Vol. 15: 297-329 (1985), the entirety of which is hereby incorporated by reference. Briefly, the tubes are pretreated with 0.2% (v/v) glutaraldehyde in 100 mM sodium phosphate buffer, pH 5.0, for 4 hours at room temperature. The tubes are then washed twice with the same buffer and an antibody solution, which is prepared by adding 2-10 ug/mL in 100 mM sodium phosphate buffer, pH 8.0, is poured into the tubes and allowed to incubate for 3 hours at 37° C. After incubation, the tubes are washed twice with 0.9% NaCl. After washing, 100 mM lysine in sodium phosphate buffer, pH 8.0, is placed in the tubes for 1 hour at 37° C. to block any remaining free aldehydes on the sides of the tubes. The tubes are then washed with several changes of PBS containing 0.05% Tween™ 20. The assembly and evacuation of the tubes is then completed as is standard in the art.

Example 2

Collection of Blood in Coated Tubes

Blood is drawn from a patient and collected in the coated evacuated tubes as prepared in Example 1. The blood is allowed to incubate in the tube at room temperature for approximately 5-90 minutes (depending on the affinity and concentration the antibody used in coating the tubes), while the tubes are gently rocked or otherwise mixed to allow binding of albumin to the antibodies on the sides of the tubes. The tubes can be incubated overnight at room temperature.

Example 3

Testing the Ability of the Coated Tubes to Remove Albumin or Other Interfering Proteins The blood collected in Example 2 is then centrifuged at 1100 G for about 10 minutes to separate the components. After component separation, the proteins in the albumin-depleted plasma is subjected to 2D gel, as described in Celis, J E, and Bravo, R, (Eds.), *Two-Dimensional gel Electrophoresis of Proteins*, Academic Press (1984), the entirety of which is hereby incorporated by reference. 2D gel electrophoresis will separate the remaining proteins in the sample, based on molecular weight and isoelectric point. The separated proteins are then isolated and purified using the Montage In-Gel Digest$_{96}$ Kit™ (Millipore Corp.) according to the manufacturer's protocol. Proteins of interest are identified using Matrix-assisted laser desorption/ionisation-time of flight mass spectrometry (MALDI-TOF MS) on an Axima CFR MALDI-TOF Mass Spectrometer (Kratos Analytical, Inc.), as described in Worrall, T A, et al., Anal. Chem. 70: 750 (1998), or using liquid chromatography.

The amount of recovery of the protein of interest can be adjusted by varying the concentration and/or affinity of the antibody used in Example 1.

Example 4

Covalent Linkage of Antibodies to Polystyrene Beads

Add 5 mL of 12.5% (v/v) glutaraldehyde in 50 mM sodium phosphate, pH 7.0, to about 25 hydrazide derivatized polystyrene beads (6.4 mm diameter; Pierce Chemical Company) and shake very gently for about 2 hours at room temperature. The beads are then washed in a Buchner funnel (without filter paper) with 100 mL water and with 20 mL of 100 mM sodium phosphate buffer, pH 6.0. Next, the glutaraldehyde-activated beads are placed in an antibody solution prepared by dissolving 2.5 mg Ab in 5 mL of sodium phosphate buffer, pH 6.0. After the beads are in the Ab solution, add 1 mg NaCNBH$_3$ to the solution. Shake gently overnight at room temperature. After shaking, the beads are washed with 100 mL of 100 mM sodium phosphate buffer, pH 6.0, and then washed with 50 mL of 100 mM NaHCO$_3$. The residual aldehydes on the beads are blocked by incubating the beads with 5 mL of 100 mM lysine for about 1 hour at room temperature. After incubating with lysine, the beads are washed with 100 mL of 100 mM Na$_2$CO$_3$ and with 100 mL water and dried. The Ab-coated beads can be stored dry at 4° C. The method above is disclosed in Tijssen, P., Practice and Theory of Enzyme ImmunoAssays, in Burdon, R H and Knippenberg, P H, (Eds.), *Laboratory Techniques in Biochemistry and Molecular Biology*, Elsevier Science Publishers, Vol. 15 (1985).

While various embodiments of the present invention have been described herein, it should be understood that these examples and embodiments have been presented by way of example only, and not limitation. Thus, the breadth and scope of the present invention should not be limited by any of the above-described exemplary embodiments.

What is claimed is:

1. A device for collecting blood comprising a reservoir, a mechanical density separator, and affinity molecules, wherein said affinity molecules are exposed to said blood during the time of collecting said blood, and wherein said affinity molecules are covalently linked to said reservoir.

2. The device of claim 1, wherein said affinity molecules are completely contained within said reservoir.

3. The device of claim 2, wherein said reservoir comprises at least one insert.

4. The device of claim 3, wherein said at least one insert comprises said affinity molecules.

5. The device of claim 4, wherein said at least one insert is a paddle.

6. The device of claim 4, wherein said affinity molecules have an affinity towards undesired targets.

7. The device of claim 4, wherein said affinity molecules have an affinity towards desired targets.

8. The device of claim 4, wherein said affinity molecules are selected from the group consisting of antibodies, antibody fragments, enzymes, fragments of enzymes, enzyme substrates, fragments of enzyme substrates, nucleotides, oligonucleotides, polynucleotides, receptors, aptamers, nanobodies, fragments of receptors, ligands, fragments of enzymes, other proteins, amino acids, peptides, polypeptides, oligopeptides, saccharides, disaccharides, polysaccharides, glycoproteins, proteoglycans, and natural and synthetic polymers.

9. The device of claim 8, wherein said affinity molecules are antibodies or fragments thereof.

10. The device of claim 9, wherein said antibody or fragment thereof binds at least one protein within said blood.

11. The device of claim 10, wherein said at least one protein is selected from the group consisting of albumin, immunoglobulins, fibrinogen, protease inhibitors, antichymotrypsin, antithrombin, macroglobulins, inter-alpha-trypsin inhibitor, C1 inhibitor, plasmin inhibitor, heparin cofactor II, tranferrin, immunoglobulin M, haptoglobin complement and alpha-1 antitrypsin.

12. The device of claim 11, wherein said protein is albumin.

13. The device of claim 2, wherein said affinity molecules are covalently linked onto the interior of said reservoir.

14. The device of claim 13, wherein said affinity molecules are covalently linked onto the interior of side walls of said reservoir.

15. The device of claim 14, wherein said interior side walls are ridged.

16. The device of claim 13, wherein said affinity molecules have an affinity towards undesired targets.

17. The device of claim 13, wherein said affinity molecules have an affinity towards desired targets.

18. The device of claim 13, wherein said affinity molecules are selected from the group consisting of antibodies, antibody fragments, enzymes, fragments of enzymes, enzyme substrates, fragments of enzyme substrates, nucleotides, oligonucleotides, polynucleotides, receptors, aptamers, nanobodies, fragments of receptors, ligands, fragments of enzymes, other proteins, amino acids, peptides, polypeptides, oligopeptides, saccharides, disaccharides, polysaccharides, glycoproteins, proteoglycans, and natural and synthetic polymers.

19. The device of claim 18, wherein said affinity molecules are antibodies or fragments thereof.

20. The device of claim 19, wherein said antibody or fragment thereof binds at least one protein within said blood.

21. The device of claim 20, wherein said at least one protein is selected from the group consisting of albumin, immunoglobulins, fibrinogen, protease inhibitors, antichymotrypsin, antithrombin, macroglobulins, inter-alpha-trypsin inhibitor, C1 inhibitor, plasmin inhibitor, heparin cofactor II, tranferrin, immunoglobulin M, haptoglobin complement and alpha-1 antitrypsin.

22. The device of claim 21, wherein said protein is albumin.

23. A method of collecting blood, comprising:
collecting blood comprising a target component;
exposing said blood to affinity molecules during the time of said collection;
allowing said affinity molecules to bind to said target component;
separating density phases of said blood collection through the use of a mechanical density separator; and
extracting a portion of said blood that has been depleted of said target component by said binding of said affinity molecules to said target component.

24. The method of claim 23, wherein establishing venous access through use of a blood collection device initiates the time of said collection.

25. The method of claim 23, wherein said affinity molecules are selected from the group consisting of antibodies, antibody fragments, enzymes, fragments of enzymes, enzyme substrates, fragments of enzyme substrates, nucleotides, oligonucleotides, polynucleotides, receptors, aptamers, nanobodies, fragments of receptors, ligands, fragments of enzymes, other proteins, amino acids, peptides, polypeptides, oligopeptides, saccharides, disaccharides, polysaccharides, glycoproteins, proteoglycans, and natural and synthetic polymers.

26. The method of claim 25, wherein said affinity molecules are antibodies or fragments thereof.

27. The method of claim 26, wherein said antibody or fragment thereof binds at least one protein within said blood.

28. The method of claim 27, wherein said at least protein is selected from the group consisting of albumin, immunoglobulins, fibrinogen, protease inhibitors, antichymotrypsin, antithrombin, macro globulins, inter-alpha-trypsin inhibitor, C1 inhibitor, plasmin inhibitor, heparin cofactor II tranferrin, immunoglobulin M, haptoglobin complement and alpha-1 antitrypsin.

29. The method of claim 28, wherein said protein is albumin.

30. The method of claim 23, comprising wherein said affinity molecules are completely enclosed within a reservoir.

31. The method of claim 30, wherein said reservoir comprises at least one insert.

32. The method of claim 31, wherein said at least insert comprises said affinity molecules.

33. The method of claim 32, wherein said affinity molecules are selected from the group consisting of antibodies, antibody fragments, enzymes, fragments of enzymes, enzyme substrates, fragments of enzyme substrates, nucleotides, oligonucleotides, polynucleotides, receptors, aptamers, nanobodies, fragments of receptors, ligands, fragments of enzymes, other proteins, amino acids, peptides, polypeptides, oligopeptides, saccharides, disaccharides, polysaccharides, glycoproteins, proteoglycans, and natural and synthetic polymers.

34. The method of claim 33, wherein said affinity molecules are antibodies or fragments thereof.

35. The method of claim 34, wherein said antibody or fragment thereof binds at least one protein within said blood.

36. The method of claim 35, wherein said at least one protein is selected from the group consisting of albumin, immunoglobulins, fibrinogen, protease inhibitors, antichymotrypsin, antithrombin, macroglobulins, inter-alpha-trypsin inhibitor, C1 inhibitor, plasmin inhibitor, heparin cofactor II, tranferrin, immunoglobulin M, haptoglobin complement and alpha-1 antitrypsin.

37. The method of claim 36, wherein said protein is albumin.

38. A method for collecting a biological fluid sample from a patient, comprising: a) providing an evacuated sample collection reservoir comprising affinity molecules and a mechanical density separator, wherein said affinity molecules are covalently linked to said reservoir; and b) exposing said biological fluid from said patient to said sample collection reservoir.

39. The method of claim 38, wherein said affinity molecules target at least two molecules selected from the group consisting of albumin, Immunoglobulin G (IgG), transferrin, Immunoglobulin A (IgA), Immunoglobulin M (IgM), and $\alpha$1-antitrypsin.

40. The method of claim 39, wherein said target molecules are IgG and albumin.

41. The method of claim 38, wherein said evacuated sample collection reservoir comprises an additive selected from the group consisting of a protease inhibitor, ethylenediaminetetraacetic acid (EDTA), sodium citrate, heparin, and a clotting factor.

42. The method of claim 38, wherein a gel electrophoresis of the exposed fluid exhibits visually distinct results compared to an identical gel electrophoresis of the identical fluid exposed to an identical evacuated sample collection container free of the affinity molecules.

\* \* \* \* \*

UNITED STATES PATENT AND TRADEMARK OFFICE
CERTIFICATE OF CORRECTION

PATENT NO.       : 8,603,345 B2                                              Page 1 of 1
APPLICATION NO.  : 10/544886
DATED            : December 10, 2013
INVENTOR(S)      : Ross et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1394 days.

Signed and Sealed this

Twenty-second Day of September, 2015

Michelle K. Lee
*Director of the United States Patent and Trademark Office*